(12) United States Patent
Takahashi et al.

(10) Patent No.: US 6,429,316 B1
(45) Date of Patent: *Aug. 6, 2002

(54) PROCESS FOR PREPARING PYRROLIDONE DERIVATIVE

(75) Inventors: Kazunari Takahashi; Yoko Seto; Masaru Utsunomiya; Souichi Orita; Kazutaka Maruyama; Tomonori Okubi, all of Okayama (JP)

(73) Assignee: Mitsubishi Chemical Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/447,237

(22) Filed: Nov. 23, 1999

(30) Foreign Application Priority Data

Nov. 24, 1998 (JP) .......................................... 10-332308
Aug. 18, 1999 (JP) .......................................... 11-231520

(51) Int. Cl.$^7$ .......................................... C07D 207/46

(52) U.S. Cl. ....................................... 548/530

(58) Field of Search ......................................... 548/530

(56) References Cited

FOREIGN PATENT DOCUMENTS

| JP | 47-18751 | * | 5/1972 |
| JP | 6-78305 | * | 10/1994 |

OTHER PUBLICATIONS

Chemical Abstracts, vol. 112, No. 11, Mar. 12, 1990, AN 98377g, JP 01 190667, Jul. 31, 1989.
Chemical Abstract, vol. 124, No. 11, Mar. 11, 1996, AN 145893g, CN 1 104 635, Jul. 5, 1995.
Derwent Publications, AN 1998–393443, JP 10 158238, Jun. 16, 1998.
JP 01190667 to Mitsubishi Chemical Industries Ltd. (Otake et al.)—Translation, Jul. 1989.*
JP 47–018751A to Teijin Corporation (Akimbo et al.)—Translation, Jul. 1989.*

* cited by examiner

*Primary Examiner*—Ceila Chang
*Assistant Examiner*—Andrea D. Small
(74) *Attorney, Agent, or Firm*—Oblon, Spivak, McClelland, Maier & Neustadt, P.C.

(57) ABSTRACT

Disclosed is a process for preparing a pyrrolidone derivative, which comprises allowing at least one of γ-butyrolactone, 4-hydroxybutyric acid, and a low-molecular polymer of 4-hydroxybutyric acid to react with an alkylamine, wherein (i) the content of a primary amine in said alkylamine is 85% by weight or lower, and (ii) the molar ratio of the total amount of the charged primary and secondary amines to the total amount of the charged γ-butyrolactone, 4-hydroxybutyric acid, and low-molecular 4-hydroxybutyric acid polymers satisfies formula:

$$1.0 \leq (A_1 + A_2/2.5)/(B_1 + B_2 + B_3)$$

wherein $A_1$, $A_2$, $B_1$, $B_2$, and $B_3$ represent the molar amounts of a primary amine, a secondary amine, γ-butyrolactone, 4-hydroxybutyric acid, and low-molecular 4-hydroxybutyric acid polymers, respectively.

13 Claims, No Drawings

PROCESS FOR PREPARING PYRROLIDONE DERIVATIVE

FIELD OF THE INVENTION

This invention relates to a process for preparing a pyrrolidone derivative. More particularly, it relates to an improvement in the process of preparing an N-alkyl-2-pyrrolidone comprising the reaction between γ-butyrolactone, etc. and alkylamines.

Pyrrolidone derivatives are used as heat-resistant solvents in various industrial processes, for example, as a metal cleaner or a solvent for functional polymers, and have recently been increasing the demand.

BACKGROUND OF THE INVENTION

Pyrrolidone derivatives, such as an N-alkyl-2-pyrrolidone, are generally prepared on an industrial scale by the reaction between a monoalkylamine and γ-butyrolactone. The starting monoalkylamine is industrially prepared by isolation from a mixture of a trialkylamine, a dialkylamine, and a monoalkylamine which is obtained by dehydration reaction between a corresponding alkanol and ammonia.

Use of the mixture of a trialkylamine, a dialkylamine, and a monoalkylamine as a starting material instead of a monoalkylamine is also proposed as disclosed in JP-B-47-18751. According to this technique, however, the amounts of the alkylamines and γ-butyrolactone added do not satisfy formula:

$$1.0 \leq (A_1 + A_2/2.5)/(B_1 + B_2 + B_3)$$

wherein $A_1$, $A_2$, $B_1$, $B_2$, and $B_3$ represent the molar amounts of a primary amine, a secondary amine, γ-butyrolactone, 4-hydroxybutyric acid, and low-molecular 4-hydroxybutyric acid polymers, respectively. Further, the yield and reaction rate achieved are lower than in starting with a monoalkylamine alone.

JP-B-6-78305 proposes a process in which monomethylamine is used in excess, and a mixture of the monoalkylamine, a trialkylamine, a dialkylamine, and ammonia resulting from isomerization of the unreacted monomethylamine during the reaction is recovered and recycled to the reaction system, which is replenished with fresh monomethylamine. In this process, however, the monomethylamine content in the alkylamine apparently exceeds 85% by weight, which is industrially unfavorable as compared with the process using a mixed amine.

SUMMARY OF THE INVENTION

It is an object of the present invention to provide a process for preparing a pyrrolidone derivative easily and in high yield by using, as one of starting materials, a primary, secondary or tertiary amine or a mixture thereof, particularly the mixed amine obtained in alkylamine production from ammonia and an alkanol.

As a result of extensive investigations, the present inventors have found that γ-butyrolactone reacts with a mixed alkylamine in a specific ratio to give a pyrrolidone derivative in as high a yield (e.g., 90% or more) as in using a monoalkylamine.

The gist of the invention lies in a process for preparing a pyrrolidone derivative which comprises allowing at least one of γ-butyrolactone, 4-hydroxybutyric acid, and a low-molecular polymer of 4-hydroxybutyric acid to react with an alkylamine, wherein (i) the content of a primary amine in the alkylamine is 85% by weight or lower, and (ii) the molar ratio of the total amount of the charged primary and secondary amines to the total amount of the charged γ-butyrolactone, 4-hydroxybutyric acid, and low-molecular 4-hydroxybutyric acid polymers satisfies formula:

$$1.0 \leq (A_1 + A_2/2.5)/(B_1 + B_2 + B_3)$$

wherein $A_1$, $A_2$, $B_1$, $B_2$, and $B_3$ represent the molar amounts of a primary amine, a secondary amine, γ-butyrolactone, 4-hydroxybutyric acid, and low-molecular 4-hydroxybutyric acid polymers, respectively.

PREFERRED EMBODIMENTS OF THE INVENTION

One of the starting materials used in the process of the invention is selected from γ-butyrolactone, 4-hydroxybutyric acid, and a low-molecular polymer of 4-hydroxybutyric acid. The term "low-molecular" as used in the specification and claims is intended to mean "to have a degree of polymerization of about 2 to 10". These starting materials can be used either individually or as a mixture thereof. A mixture resulting from an equilibrium reaction in the presence of water is also employable.

The alkylamine, the other starting material used in the invention, can be a mixture of at least two of a primary amine, a secondary amine and a tertiary amine, or a primary or secondary amine could be used alone.

The alkyl moiety in the alkylamines maybe cyclic or acyclic, either straight or branched, and may be saturated or unsaturated. The alkyl moieties in a secondary or tertiary amine may be either the same or different. It is preferred that the alkyl moiety be a saturated and straight-chain alkyl group and that the two or three alkyl groups in a secondary or tertiary amine be the same. While not limiting, the number of the carbon atoms in the alkyl group is preferably 1 to 20, still preferably 1 to 10, and particularly preferably 1 to 3.

Examples of the primary amines are methylamine, ethylamine, and propylamine; the secondary amines are dimethylamine, diethylamine, dipropylamine, methylethylamine, methylpropylamine, and ethylpropylamine; and the tertiary amines are trimethylamine, triethylamine, tripropylamine, dimethylethylamine, dimethylpropylamine, diethylmethylamine, diethylpropylamine, dipropylmethylamine, and dipropylethylamine. Preferred of them are methylamine as a primary amine, dimethylamine as a secondary amine, and trimethylamine as a tertiary amine.

Where mixed amines are used, the mixing ratio can be the ratio of mixed amines that are generally obtained in industry, i.e., 20 to 40% by weight of a primary amine, 50 to 75% by weight of a secondary amine, and 5 to 10% by weight of a tertiary amine, although the mixing ratio is not limited thereto. For the economical standpoint, to use mixed amines having the mixing ratio in the above range is more advantageous than to use a primary, secondary or tertiary amine alone. From the standpoint of reaction rate, however, a primary amine is preferred to a tertiary amine. Taking these points into consideration, it is desirable that the primary amine content in the starting alkylamine be 85% by weight or lower, preferably 20% to 85% by weight, more preferably 40% to 85% by weight.

It is required for obtaining pyrrolidone derivatives in high yield that the alkylamine be used in such an amount that the molar ratio of the total amount of the primary and secondary amines to the total amount of the γ-butyrolactone, 4-hydroxybutyric acid, and low-molecular 4-hydroxybutyric acid polymers, which ratio is represented by formula:

$$(A_1+A_2/2.5)/(B_1+B_2+B_3) \leq 10$$

wherein $A_1$, $A_2$, $B_1$, $B_2$, and $B_3$ represent the charged amount (mole number) of a primary amine, a secondary amine, γ-butyrolactone, 4-hydroxybutyric acid, and low-molecular 4-hydroxybutyric acid polymers, respectively, and will be referred to as "parameter value", be 1.0 or greater. If the starting compounds are used in amounts giving the parameter value of smaller than 1.0, disadvantages can result, such as reduction in conversion of γ-butyrolactone or reduction in selectivity to the desired pyrrolidone derivative.

While not limiting, the upper limit of the parameter value is usually 10.0, preferably 5.0. With the parameter value below this, an excessive load can be avoided in the step of recovering and recycling the alkylamine.

The reaction is preferably carried out in the presence of water. Water is usually used in an amount of 0.5 to 20 mol, preferably 2 to 10 mol, still preferably 3 to 5 mol, per mole of the total amount of γ-butyrolactone, 4-hydroxybutyric acid, and low-molecular 4-hydroxybutyric acid polymers. With the amount of water being in an appropriate range, the reaction rate increases, and the reverse reaction from the produced pyrrolidone derivative to the starting γ-butyrolactone can be suppressed.

The reaction temperature is usually in the range of from 190° to 350° C. From the viewpoint of purity, tone, etc. of the product, the reaction temperature is preferably from 220 to 350° C., still preferably from 230 to 300° C., particularly preferably from 235 to 275° C.

The reaction pressure is not particularly limited. The reaction may be at atmospheric pressure or reduced pressure or under pressure. Usually, the reaction is conveniently performed under the pressure generated under the adopted reaction conditions, i.e., the total pressure of the reactants and the product which is decided by the temperature, the reactor capacity, the amounts of the starting materials, and the like. Gas inert to the reaction, for example nitrogen or argon, may be present in the reactor. The reaction time is usually 0.1 to 20 hours, preferably 0.5 to 10 hours, while depending on the temperature, pressure, etc.

The process of the invention can be carried out in the presence of a carboxylic acid, a carboxylic acid ester or a carboxylic acid amide other than the 4-hydroxybutyric acid or low-molecular polymers thereof derived from γ-butyrolactone. Such carboxylic acid compounds include carboxylic acids, e.g., formic acid, acetic acid, propionic acid, butyric acid, enanthic acid, succinic acid, and maleic acid; carboxylic esters, e.g., methyl formate, methyl acetate, methyl propionate, methyl butyrate, methyl enanthate, methyl succinate, methyl maleate, ethyl acetate, and butyl acetate; and carboxylic acid amides, e.g., N,N-dimethylformamide, N,N-dimethylacetamide, N-methylacetamide, N,N-dimethylpropionamide, N,N-dimethylbutyramide, and N,N-dimethylenanthamide. Of these carboxylic acid compounds, preferred are acetic acid as a carboxylic acid; methyl acetate as a carboxylic ester; and N,N-dimethylacetamide and N-methylacetamide as a carboxylic acid amide.

These carboxylic acid compounds can be used either individually or as a combination of two or more thereof. While not limiting, they can be present in a total amount usually of 0.005 to 1 mol, preferably 0.01 to 0.5 mol, still preferably 0.02 to 0.3 mol, per mole of the total amount of γ-butyrolactone, 4-hydroxybutyric acid and low-molecular 4-hydroxybutyric acid polymers.

The invention will now be illustrated in greater detail with reference to Examples and Comparative Examples, but it should be understood that the invention is not limited thereto and that modifications can be made therein without departing from the scope of the invention. Unless otherwise noted, all the percents are by weight.

EXAMPLE 1

In a 500 ml autoclave equipped with an induction stirrer were charged 120.0 g (1.40 mol) of γ-butyrolactone, 46.2 g (1.49 mol) of 100% monomethylamine, 110.0 g of a 50% aqueous solution of dimethylamine (1.24 mol), and 11.0 g (0.19 mol) of 100% trimethylamine, and 45.44 g of water and allowed to react at 270° C. for 5 hours. The pressure was maintained at 71 kgf/cm$^2$ during the reaction.

The primary amine content in the alkylamine was 41%. The parameter value was 1.42. The total amount of water in the reaction system was 4.0 mol per mole of the total amount of γ-butyrolactone, 4-hydroxybutyric acid, and low-molecular 4-hydroxybutyric acid polymers.

After the reaction, the autoclave was cooled, and the reaction product was analyzed by gas chromatography. It was found that the yield of N-methyl-2-pyrrolidone, the desired product, was 134.4 g (1.36 mol; 97%), and the γ-butyrolactone conversion was 100%.

EXAMPLE 2

In a 500 ml autoclave equipped with an induction stirrer were charged 99.14 g (1.15 mol) of γ-butyrolactone, 74.93 g of a 40% aqueous solution containing 0.96 mol of monomethylamine, 47.26 g of a 50% aqueous solution containing 0.52 mol of dimethylamine, and 34.82 g of water and allowed to react at 270° C. for 3 hours. During the reaction, the pressure was maintained at 56 kgf/cm$^2$.

The primary amine content in the alkylamine was 56%. The parameter value was 1.02. The total amount of water in the reaction system was 5.0 mol per mole of the total amount of γ-butyrolactone, 4-hydroxybutyric acid, and low-molecular 4-hydroxybutyric acid polymers.

After the reaction, the autoclave was cooled. Chromatographic analysis on the reaction product revealed that the yield of N-methyl-2-pyrrolidone was 107.55 g (1.09 mol; 94%), and the γ-butyrolactone conversion was 100%.

COMPARATIVE EXAMPLE 1

In a 500 ml autoclave equipped with an induction stirrer were charged 99.60 g (1.16 mol) of γ-butyrolactone, 80.88 g of a 40% aqueous solution containing 1.04 mol of monomethylamine, 10.44 g of a 50% aqueous solution containing 0.12 mol of dimethylamine, and 50.53 g of water and allowed to react at 270° C. for 3 hours. During the reaction, the pressure was maintained at 49 kgf/cm$^2$.

The primary amine content in the alkylamine was 86%. The parameter value was 0.94. The total amount of water in the reaction system was 5.0 mol per mole of the total amount of γ-butyrolactone, 4-hydroxybutyric acid, and low-molecular 4-hydroxybutyric acid polymers.

After the reaction, the autoclave was cooled. Chromatographic analysis on the reaction product revealed that the yield of N-methyl-2-pyrrolidone was 92.85 g (0.94 mol; 81%), and the γ-butyrolactone conversion was 97%.

EXAMPLE 3

In a 500 ml autoclave equipped with an induction stirrer were charged 77 g (0.9 mol) of γ-butyrolactone, 30.65 g of 100% monomethylamine, 76.5 g of a 50% aqueous solution containing 0.85 mol of dimethylamine, 7.66 g of 100% trimethylamine, 13.33 g (0.18 mol) of methyl acetate, and 26.55 g of water and allowed to react at 255° C. for 5 hours. During the reaction, the pressure was maintained at 55 kgf/cm².

The primary amine content in the alkylamine was 45%. The parameter value was 1.5. The total amount of water in the reaction system was 4.0 mol per mole of the total amount of γ-butyrolactone, 4-hydroxybutyric acid, and low-molecular 4-hydroxybutyric acid polymers.

After the reaction, the autoclave was cooled. Chromatographic analysis on the reaction product revealed that the yield of N-methyl-2-pyrrolidone was 84.55 g (0.854 mol; 94.9%), and the γ-butyrolactone conversion was 100%.

EXAMPLE 4

In a 500 ml autoclave equipped with an induction stirrer were charged 100 g (1.16 mol) of γ-butyrolactone, 67.84 g of a 40% aqueous solution containing 0.88 mol of monomethylamine, 67.84 g of a 50% aqueous solution containing 0.75 mol of dimethylamine, 6.78 g of 100% trimethylamine, 20.21 g (0.23 mol) of N,N-dimethylacetamide, and 6.78 g of water and allowed to react at 255° C. for 2 hours. During the reaction, the pressure was maintained at 50 kgf/cm².

The primary amine content in the alkylamine was 40%. The parameter value was 1.02. The total amount of water in the reaction system was 3.9 mol per mole of the charged γ-butyrolactone.

After the reaction, the autoclave was cooled. Chromatographic analysis on the reaction product revealed that the yield of N-methyl-2-pyrrolidone was 106.6 g (1.09 mol; 93.8%), and the γ-butyrolactone conversion was 98%.

According to the invention, an N-alkyl-2-pyrrolidone can be prepared in high yield by allowing an alkylamine and γ-butyrolactone to react at a specific ratio.

What is claimed is:

1. A process for preparing a pyrrolidone derivative, which comprises allowing at least one of γ-butyrolactone, 4-hydroxybutyric acid, and a low-molecular weight polymer of 4-hydroxybutyric acid to react with an alkylamine, wherein (i) said alkylamine has a content of primary amine of from 20% to 85% by weight, and (ii) a molar ratio of total primary and secondary amines charged to total γ-butyrolactone, 4-hydroxybutyric acid, and low-molecular weight polymer of 4-hydroxybutyric acid charged satisfies formula:

$$1.0 \leq (A_1 + A_2/2.5)/(B_1 + B_2 + B_3)$$

wherein $A_1$, $A_2$, $B_1$, $B_2$, and $B_3$ represent the molar amounts of a primary amine, a secondary amine, γ-butyrolactone, 4-hydroxybutyric acid, and a low-molecular weight polymer of 4-hydroxybutyric acid, respectively.

2. The process according to claim 1, wherein the molar ratio of total primary and secondary amines charged to total γ-butyrolactone, 4-hydroxybutyric acid, and low-molecular weight polymer of 4-hydroxybutyric acid charged satisfies formula;

$$1.0 \leq (A_1 + A_2/2.5)/(B_1 + B_2 + B_3)$$

wherein $A_1$, $A_2$, $B_2$, and $B_3$ are as defined above.

3. The process according to claim 1, wherein the molar ratio of total primary and secondary amines charged to total γ-butyrolacotne, 4-hydroxybutyric acid, and low-molecular weight polymer of 4-hydroxybutyric acid charged satisfies formula:

$$1.0 \leq (A_1 + A_2/2.5)/(B_1 + B_2 + B_3) \leq 5$$

wherein $A_1$, $A_2$, $B_1$, $B_2$, and $B_3$ are as defined above.

4. The process according to claim 1, wherein said pyrrolidone derivative is an N-alkyl-2-pyrrolidone.

5. The process according to claim 1, wherein the reaction is carried out in the presence of a carboxylic acid, a carboxylic acid ester or a carboxylic acid amide other than 4-hydroxybutyric acid or low-molecular weight polymers thereof derived from γ-butyrolactone.

6. The process according to claim 5, wherein said carboxylic acid, said carboxylic acid ester or said carboxylic acid amide is acetic acid, an acetic acid ester or an acetic acid amide.

7. The process according to claim 1, wherein the alkyl moiety of said alkylamine has 3 or less carbon atoms.

8. The process according to claim 1, wherein the reaction is carried out in the presence of 2 to 10 mol of water per mole of the total amount of γ-butyrolactone, 4-hydroxybutyric acid, and low-molecular weight polymer of 4-hydroxybutyric acid at a temperature of 220 to 350° C.

9. The process according to claim 1, wherein said alkylamine is at least two of a primary amine, a secondary amine, and a tertiary amine.

10. The process of claim 1, wherein the reaction is carried out in the presence of from 0.5 to 20 mol of water per mole of the total amount of γ-butyrolactone, 3-hydroxybutytric acid, and low-molecular 4-hydroxybutyric acid polymers.

11. The process of claim 8, wherein the amount of water is from 3 to 5 mol per mole of the total amount of γ-butyrolactone, 3-hydroxybutyric acid, and low-molecular 4-hydroxybutyric acid polymers.

12. The process of claim 1, wherein the reaction is performed at a temperature of from 190 to 350° C.

13. The process of claim 12, wherein the reaction is performed at a temperature of from 220 to 350° C.

* * * * *